(12) United States Patent
Herman

(10) Patent No.: US 7,863,277 B1
(45) Date of Patent: Jan. 4, 2011

(54) TOPICAL ANTIPSYCHOTIC COMPOSITION

(75) Inventor: Craig Herman, Conrad, IA (US)

(73) Assignee: Medcara, L.L.C., Conrad, IA (US)

( * ) Notice: Subject to any disclaimer, the term of this patent is extended or adjusted under 35 U.S.C. 154(b) by 1131 days.

(21) Appl. No.: 11/369,638

(22) Filed: Mar. 7, 2006

Related U.S. Application Data

(63) Continuation-in-part of application No. 11/094,978, filed on Mar. 31, 2005, now abandoned.

(51) Int. Cl.
*A01N 43/00* (2006.01)
*A61K 31/553* (2006.01)
*A61K 31/554* (2006.01)
*A61K 31/497* (2006.01)
*C07D 267/02* (2006.01)
*C07D 281/02* (2006.01)
*C07D 291/08* (2006.01)
*C07D 419/00* (2006.01)
*C07D 413/00* (2006.01)

(52) U.S. Cl. .............. 514/252.13; 514/254.04; 514/211.13; 540/551; 544/368

(58) Field of Classification Search ............ 514/211.13, 514/252.13, 254.04; 540/551; 544/368
See application file for complete search history.

(56) References Cited

U.S. PATENT DOCUMENTS

| 6,290,986 | B1 * | 9/2001 | Murdock et al. | 424/449 |
| 7,666,914 | B2 * | 2/2010 | Richlin et al. | 514/23 |
| 2002/0192300 | A1 * | 12/2002 | Luo et al. | 424/719 |
| 2003/0180352 | A1 * | 9/2003 | Patel et al. | 424/465 |

OTHER PUBLICATIONS

Yesook, Inclusion Complexation of Ziprasidone Mesylate with B-Cyclodextrin Sulfobutyl Ether, J. Pharm. Sci., Dec. 1998, vol. 87, No. 12, Publisher unknown.

* cited by examiner

*Primary Examiner*—Sreeni Padmanabhan
*Assistant Examiner*—Kara R McMillian
(74) *Attorney, Agent, or Firm*—Nyemaster Law Firm; Wendy K. Marsh

(57) ABSTRACT

A transdermal composition that contains an antipsychotic is provided for the treatment of neuropsychiatric disorders. Also, provided are methods for preparing a topical antipsychotic composition. Methods for treating neuropsychiatric disorders, including schizophrenia, are further disclosed. The transdermal composition includes a therapeutically effective amount of an antipsychotic in an amount sufficient to treat neuropsychiatric disorders in a pharmaceutically acceptable carrier.

4 Claims, No Drawings

TOPICAL ANTIPSYCHOTIC COMPOSITION

CROSS-REFERENCE TO RELATED APPLICATION

The present application is a continuation-in-part of U.S. Ser. No. 11/094,978 filed Mar. 31, 2005, the disclosure of which is expressly incorporated herein by reference.

BACKGROUND OF THE INVENTION

Schizophrenia is one of the most severe and debilitating of the major psychiatric diseases. It usually starts in late adolescence or early adult life and often becomes chronic and disabling. Men and women are at equal risk of developing this illness; however, most males become ill between 16 and 25 years old, while females develop symptoms between 25 and 30. People with schizophrenia often experience both "positive" symptoms (e.g., delusions, hallucinations, disorganized thinking, and agitation) and "negative" symptoms (e.g., lack of drive or initiative, social withdrawal, apathy, and emotional unresponsiveness).

Schizophrenia affects 1% of the world population. There are an estimated 45 million people with schizophrenia in the world, with more than 33 million of them in the developing countries. This disease places a heavy burden on the patient's family and relatives, both in terms of the direct and indirect costs involved and the social stigma associated with the illness, sometimes over generations. Such stigma often leads to isolation and neglect.

Moreover, schizophrenia accounts for one fourth of all mental health costs and takes up one in three psychiatric hospital beds. Most schizophrenia patients are never able to work. The cost of schizophrenia to society is enormous. In the United States, for example, the direct cost of treatment of schizophrenia has been estimated to be close to 0.5% of the gross national product. Standardized mortality ratios (SMRs) for schizophrenic patients are estimated to be two to four times higher than the general population, and their life expectancy overall are 20% shorter than for the general population. The most common cause of death among schizophrenic patients is suicide (in 10% of patients) which represents a 20 times higher risk than for the general population. Deaths from heart disease and from diseases of the respiratory and digestive system are also increased among schizophrenic patients.

Bipolar disorders are relatively common disorders with severe and potentially disabling effects. In addition to the severe effects on patients' social development, suicide completion rates among bipolar patients are reported to be about 15%.

Bipolar disorders are characterized by phases of excitement and often including depression; the excitement phases, referred to as mania or hypomania, and depression can alternate or occur in various admixtures, and can occur to different degrees of severity and over varying time periods. Because bipolar disorders can exist in different forms and display different symptoms, the classification of bipolar disorder has been the subject of extensive studies resulting in the definition of bipolar disorder subtypes and widening of the overall concept to include patients previously thought to be suffering from different disorders. Bipolar disorders often share certain clinical signs, symptoms, treatments and neurobiological features with psychotic illnesses in general and therefore present a challenge to the psychiatrist to make an accurate diagnosis. Furthermore, because the course of bipolar disorders and various mood and psychotic disorders can differ greatly, it is critical to characterize the illness as early as possible in order to offer means to manage the illness over a long term.

Bipolar disorders appear in about 1.3% of the population and have been reported to constitute about half of the mood disorders seen in a psychiatric clinic. Bipolar disorders have been found to vary with gender depending of the type of disorder; for example, bipolar disorder I is found equally among men and women, while bipolar disorder II is reportedly more common in women. The age of onset of bipolar disorders is typically in the teenage years and diagnosis is typically made in the patient's early twenties. Bipolar disorders also occur among the elderly, generally as a result of a medical or neurological disorder.

The costs of bipolar disorders to society are enormous. The mania associated with the disease impairs performance and causes psychosis, and often results in hospitalization. This disease places a heavy burden on the patient's family and relatives, both in terms of the direct and indirect costs involved and the social stigma associated with the illness, sometimes over generations. Such stigma often leads to isolation and neglect. Furthermore, the earlier the onset, the more severe are the effects of interrupted education and social development.

As there are currently no cures for schizophrenia, bipolar disorders, or other neuropsychiatric disorders, the objective of treatment is to reduce the severity of the symptoms, if possible to the point of remission, in an effective manner.

For these and other reasons, there is a need for the present invention.

Accordingly, it is a primary object of the present invention to provide a composition effective for the treatment of neuropsychiatric disorders.

Accordingly, it is an object of the present invention to provide a transdermal composition effective for the treatment of neuropsychiatric disorders.

Another object of the present invention is to provide a transdermal composition that is quickly absorbed.

Still another object of the present invention is to provide a method using a transdermal composition effective for the treatment of neuropyschiatric disorders.

A further object of the present invention is to provide an effective treatment of neuropyschiatric disorders that does not pose a risk to health care workers and is less invasive to the patient.

The method and means of accomplishing each of the above objectives as well as others will become apparent from the detailed description of the invention which follows hereafter.

BRIEF SUMMARY OF THE INVENTION

The invention is based upon the unexpected observation that a transdermal composition containing an antipsychotic is effective in treating neuropsychiatric disorders. Methods of treating neuropsychiatric disorders of a patient are provided. A therapeutically effective amount of a transdermal composition comprising an antipsychotic is topically applied to a patient. A method for the preparation of a transdermal composition comprising an antipsychotic is also provided. The composition is prepared by mixing an antipsychotic with a pharmaceutically acceptable carrier to form a mixture suitable for topical application.

The method and means of accomplishing each of the above objectives as well as others will become apparent from the detailed description of the invention, which follows hereafter.

DETAILED DESCRIPTION OF THE PREFERRED EMBODIMENT

The present inventor has found that applying an antipsychotic as a transdermal composition provides a novel approach for treating neuropsychiatric disorders, especially schizophrenia. This invention relates to transdermal compositions containing one or more antipsychotics. The invention is primarily concerned with such compositions and methods for human therapeutic use.

The permeability barrier provided by normal skin is that as molecules reach a molecular weight of around 500 Daltons there is a rapid decline in permeability. The molecular weight of ziprasidone, and other antipsychotics, closely approach this 500 Dalton limit. For this reason, they have been traditionally dismissed as being suitable for topical administration.

Several factors determine the permeability of the skin to administered agents. These factors include the characteristics of the treated skin, characteristics of the delivery agent, the lipophilicity of the drug, melting points of the drug, hydrogen-bonding capability of the drug, and tendency of the drug to ionize. With respect to the drug-related factors, these all weigh against successful topical administration of antipsychotic medications.

Ziprasidone is a well-known antipsychotic used for treating various psychoses. Pfizer sells an oral formulation of ziprasidone hydrochloride under the trade name Geodon®. Ziprasidone, or 5-(2-(4-(1,2-benzisothiazol-3-yl)piperazinyl)ethyl)-6-chloro-1,3-dihydro-2(1H)-indole-2-one, is a benzothiazolylpiperazine with the chemical formula $C_{21}H_{21}CN_4OH.HCl)_2H_2O$. Ziprasidone is believed to reduce symptoms of schizophrenia by blocking the action of serotonin and dopamine, two neurotransmitter chemicals, at specific receptors in the brain. Ziprasidone is further believed to inhibit the reuptake of serotonin and norepinephrine into brain cells, thereby improving depressive symptoms in people with schizophrenia.

Regardless of the mechanism, studies have shown that ziprasidone is effective in controlling negative symptoms along with the positive symptoms of schizophrenia when administered either orally or intramuscularly with few side effects. It has been widely suggested that ziprasidone may potentially be used to treat a wide array of disorders characterized by psychotic episodes, psychosis, acute mania, mild anxiety and depression, including schizophrenia, bipolar disorders, acute mania, depression, Tourette's syndrome bulimia, dementia, and autism.

Ziprasidone (i.e. Geodon®) is routinely prescribed for oral administration by the patient. However, the oral bioavailability of ziprasidone is only about 60%, with decreasing absorption when not taken concurrently with food. Patients, however, do not always remember to take medication with food, thereby affecting the drug's absorption rate and extent of absorption, thus compromising their treatment.

An injectable version of ziprasidone hydrochloride is available that does not depend on food for absorption, but is almost exclusively used in cases for quick relief of agitated patients. However, with the advent of Human Immunodeficiency Virus (HIV) and other blood borne pathogens such as Hepatitis B Virus (HBV) and Hepatitis C Virus (HCV), healthcare workers are presented with an occupational hazard of accidentally sticking themselves with a used or "dirty" needle. The chances of getting stuck increase when encountering an agitated patient. After disposal, conventional syringes may continue to pose a risk to sanitation workers and anyone else who comes in contact with landfills and waste management processes. Some syringes will undoubtedly be disposed of or handled improperly prior to disposal, increasing the chance of injury. Despite their utility, conventional syringes thus clearly pose a danger to healthcare workers.

As already noted above, it was not believed that antipsychotics could be administered topically. Contrary to popular belief, however, the inventor has surprisingly discovered that ziprasidone, and other antipsychotics, can be topically administered to provide a safer and more consistent method of obtaining efficacious levels of the drug in the bloodstream. Furthermore, this method does not rely on food to aid absorption or utilize a syringe for administration. The present method of administration is safer for health care workers and less invasive to the patient than presently used injectable forms of ziprasidone, and other antipsychotics.

As used herein the terms "ziprasidone", "antipsychotic", and "antipsychotics" refer to all forms of ziprasidone and antipsychotic medications, including their prodrugs which metabolize to the compounds and the analogues and biologically active salt forms thereof, as well as optical isomers which provide the same pharmaceutical results. While ziprasidone hydrochloride is a preferred salt form of ziprasidone as used in the instant invention, the invention contemplates administration of ziprasidone, or other antipsychotics, in any pharmaceutically effective salt form. Such salts are well known in the art and include, but are not limited to, acetate, adipate, alginate, citrate, aspartate, benzoate, benzene sulfonate, besylate, bisulfate, butyrate, camphorate, camphor sulfonate, digluconate, esylate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, mesylate, nicotinate, 2-naphthalene sulfonate, napsylate, oxalate, palmitoate, pectinate, persulfate, 3-phenylpropionate, picrate, pivalate, propionate, succinate, tartrate, thiocyanate, tosylate, phosphate, glutamate, bicarbonate, p-toluene sulfonate and undecanoate salts.

Antipsychotics are a class of pharmacological agents that are well known in the art and include, but are not limited to, olanzapine (Zyprexa®), quetiapine (Seroquel®), risperidone (Risperidal®), clozapine (Clozaril®), aripiprazole (Abilify®), chlorpromazine (Thorazine®), fluphenazine (Prolixin®), perphenazine (Trilafon®), prochlorperazine (Compazine®), thioridazine (Mellaril®), trifluorperazine (Stelazine®), haloperidol (Haldol®), pimozide (Orap®), and tetrabenazine (Nitoman®). Antipsychotics in turn are generally divided into two types: conventional and atypical.

Conventional antipsychotics were introduced in the 1950's and include chlorpromazine, fluphenazine, haloperidol, thiothixene, trifluoroperazine, perphenazine, and thioridazine. These medications primarily relieve positive symptoms of schizophrenia. Atypical antipsychotics were introduced in the last decade, and while also effective against positive symptoms, they also appear to relieve negative symptoms more effectively. The atypical antipsychotics include aripiprazole, risperidone, clozapine, olanzapine, quetiapine, and ziprasidone. The invention is intended to include all types of antipsychotics, with the exception of haloperidol, with atypical antipsychotics being preferred. Ziprasidone and quetiapine are most preferred.

As used herein the term "treatment" or "treating" includes the amelioration or elimination of the developed physical and/or mental condition once it has been established or improvement or alleviation of the characteristic symptoms of such condition.

As used here, the term "therapeutically effective amount," means that amount of the pharmaceutical composition that provides a therapeutic benefit in the treatment, prevention, or management of one or more therapeutic conditions.

The terms "pharmaceutically acceptable" or "transdermally acceptable," as used herein, means that the compositions or components thereof so described are suitable for transdermal administration through mammalian skin without undue toxicity, incompatibility, instability, allergic response, and the like.

As used herein, a "neuropsychiatric disorder" refers to acute and subacute disorders with both neurological and psychiatric features. Examples of common neuropsychiatric disorders that are treatable by the present invention include but are not limited to are schizophrenia, autism, depression, benign forgetfulness, childhood learning disorders, close head injury, attention deficit disorder, psychosis, Tourette's syndrome, bulimia, dementia, depressive disorder (MDD), bipolar disorder (manic-depressive illness or BPD), anxiety, and drug addiction including dependence, withdrawal, and drug tolerance, disorders arising from trauma, ischemic or hypoxic conditions including stroke, hypoglycemia, cerebral ischemia, cardiac arrest, spinal cord trauma, head trauma, perinatal hypoxia, cardiac arrest and hypoglycemic neuronal damage, epilepsy, Alzheimer's disease, Huntington's disease, Parkinsonism, amyotrophic lateral sclerosis, convulsion, pain, schizophrenia, muscle spasms, migraine headaches, urinary incontinence, emesis, brain edema, tardive dyskinesia, AIDS-induced dementia, ocular damage, retinopathy, cognitive disorders, and neuronal injury associated with HIV-infection such as dysfunction in cognition, movement and sensation. Additional neuropsychiatric disorders are described in Diagnostic and Statistical Manual of Mental Disorders, 4.sup.th Ed., American Psychiatric Press, (1994) and U.S. Pat. No. 6,228,875 incorporated herein by reference. The skilled artisan will recognize that additional conditions or disorders may be classified as neuropsychiatric disorders as medical scientific progress evolves.

The phrase "therapeutically effective amount" refers to the amount of ziprasidone or other antipsychotic in a transdermal composition that provides a therapeutic benefit in the management or treatment of a neuropsychiatric disorder so that an observable improvement over the baseline clinically observable signs and symptoms of a neuropsychiatric disorder. One of ordinary skill in the art would be familiar with such signs and symptoms.

It should be understood by one of ordinary skill in the art that this amount will vary depending on the drug used, disorder being treated, and the patient.

In one embodiment, the transdermal composition is prepared by forming a mixture comprising an antipsychotic and a pharmaceutically acceptable carrier. Any suitable pharmaceutically acceptable carrier may be used with the transdermal composition, as will be readily apparent to one of ordinary skill in the art.

The precise topically active agent used in the topical delivery composition of the present invention is not critical. In fact, pharmaceutically/pharmacologically active agents that are both water phase soluble and/or oil phase soluble may be used. As those skilled in the art of formulation know the precise percentage of the active will vary depending upon a number of factors, including the type of antipsychotic used, whether the antipsychotic is used in free base or salt form, severity of symptoms, etc. but, it will generally be within the range of from about 0.01 to 99% by weight antipsychotic, with about 0.05% to 25% by weight being preferred, and about 10-15% by weight is most preferred. The dosages will also vary greatly depending upon the agent to be administered, patient weight and condition, etc., but will generally range from about 0.01-1500 mg/day.

The composition may also contain other active agents that are compatible with the antipsychotic, if desired. Typical topical active agents may include, but are not limited to, analgesics, anesthetics, antihistamines, anti-inflammatory agents, antibiotics, antifungals, antivirals, antimicrobials, such as silver, silver compounds, clindamycin phosphate, erythromycin, sodium sulfacetamide, scabicides, pediculicides, antineoplastics, antiperspirants, antipruritics, antisporadics, vasoactive agents, antiseborrheics, burn actives, cauterizing agents, depigmenting agents, enzymes, kerotolytics, steroids, sunscreens, metronidazole, and retinol. In addition to the active, the composition may contain other excipients to provide it in various forms for specific product fields.

The present inventor has also determined that a beneficial effect may be derived from including a vasoactive agent, such as betahistine, papaverine, phentolamine, or other substances that facilitate capillary dilation in the skin, thus improving absorption of the ziprasidone. If included, such vasoactives should be included in the doses normally used for vasoactivity, ranging from about 0.1-1000 mg/dose.

The transdermal formulations of the present invention may be prepared in a variety of physical forms. To prepare, the antipsychotic may simply be combined with a pharmaceutically acceptable wetting agent, such as an organic solvent, to disperse the drug. The dispersed drug is then incorporated into a pharmaceutically acceptable base that will vary depending upon the topical dosage form desired. The primary topical dosage forms are solids, creams, lotions, and gels/serums. The principal differences between these forms are their physical appearance and viscosity (or thickness), which are governed primarily by the presence and amount of emulsifiers and viscosity adjusters. Moreover, a particular topical formulation may often be prepared in a variety of these forms. Solids are generally firm and non-pourable and commonly are formulated as a bar or stick, or in particulate form; solids may be opaque or transparent, and optionally may contain solvents (including water and alcohol), emulsifiers, moisturizers, emollients, fragrances, dyes/colorants, preservatives and active ingredients. Creams and lotions are often similar to one another, differing mainly in their viscosity (creams are typically thicker and more viscous than lotions); both lotions and creams may be opaque, translucent or clear and often contain emulsifiers, solvents (including water and alcohol) and viscosity adjusting agents. Lotions and creams also may optionally contain moisturizers and emollients (especially in the case of skin care products), as well as fragrances, dyes/colorants, preservatives and active ingredients. Gels/serums may be prepared with a range of viscosities, from thick (high viscosity) to thin (low viscosity) and differ principally from lotions and creams in that gels/serums are usually clear rather than opaque. Like lotions and creams, gels/serums often contain emulsifiers, solvents (including water and alcohol) and viscosity adjusters, and may also contain moisturizers and emollients, fragrances, dyes/colorants, preservatives and active ingredients. The dosage forms may be combined with various inert pharmaceutically acceptable carriers, such as transdermal patches.

Suitable viscosity adjusting agents (i.e., thickening and thinning agents) for use in the formulations of the present invention include, but are not limited to, protective colloids or non-ionic gums such as hydroxyethylcellulose (e.g., Cellosize HEC QP52,000-H, manufactured by Amerchol), xanthan gum, and sclerotium gum (Amigel 1.0), as well as magnesium aluminum silicate (Veegum Ultra), silica, microcrystalline wax, beeswax, paraffin, and cetyl palmitate. In addition, appropriate combinations or mixtures of these viscosity adjusters may be utilized according to the present invention.

Suitable additives for use in the formulations of the present invention include, but are not limited to, water, penetration enhancers such as isopropyl palmitate, ethanol, butylene glycol, propylene glycol, isopropyl alcohol, isoprene glycol, glycerin, Carbowax 200, Carbowax 400, Carbowax 600, and Carbowax 800. In addition, combinations or mixtures of these additives may be used according to the present invention.

Suitable surfactants for use in the formulations of the present invention include, but are not limited to nonionic surfactants like Surfactant 190 (dimethicone copolyol), Polysorbate 20 (Tween 20), Polysorbate 40 (Tween 40), Polysorbate 60 (Tween 60), Polysorbate 80 (Tween 80), lauramide DEA, cocamide DEA, and cocamide MEA, amphoteric surfactants like oleyl betaine and cocamidopropyl betaine (Velvetex BK-35), and cationic surfactants like Phospholipid PTC (Cocamidopropyl phosphatidyl PG-dimonium chloride), lecithin, poloxomers, and wetting agents such as ethoxy diglycol. Appropriate combinations or mixtures of such surfactants may also be used according to the present invention.

Suitable preservatives for use in the formulations of the present invention include, but are not limited to, antimicrobials such as Germaben II (manufactured by ICI; propylene glycol, diazolidinyl urea, methylparaben, and propylparaben), methylparaben, propylparaben, imidazolidinyl urea, benzyl alcohol, sorbic acid, benzoic acid, sodium benzoate, dichlorobenzyl alcohol, and formaldehyde, as well as physical stabilizers and antioxidants such as alpha-tocopherol (vitamin E), sodium ascorbate/ascorbic acid, ascorbyl palmitate and propyl gallate. In addition, combinations or mixtures of these preservatives may also be used in the formulations of the present invention.

Suitable moisturizers for use in the formulations of the present invention include, but are not limited to, lactic acid and other hydroxy acids and their salts, glycerin, propylene glycol, butylene glycol, sodium PCA, Carbowax 200, Carbowax 400, and Carbowax 800. Suitable emollients for use in the formulations of the present invention include, but are not limited to, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate). In addition, appropriate combinations and mixtures of any of these moisturizing agents and emollients may be used in accordance with the present invention.

Suitable fragrances and colors, such as FD&C Red No. 40 and FD&C Yellow No. 5, may be used in the formulations of the present invention. Other examples of fragrances and colors suitable for use in topical products are known in the art.

Other suitable additional and adjunct ingredients which may be included in the formulations of the present invention include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., CTFA Cosmetic Ingredient Handbook, 2.sup.nd edition, eds. John A. Wenninger and G. N. McEwen, Jr. (CTFA, 1992).

The inventor has also determined that ziprasidone and other antipsychotics may be formulated with cyclodextrin to form an encapsulated ziprasidone topical composition. Cyclodextrins are cyclic (α-1,4)-linked oligosaccharides of a-D-gluco-pyranose containing a relatively hydrophobic central cavity and hydrophilic outer surface. In a preferred embodiment, the composition is sulfobutylether β-cyclodextrin encapsulated ziprasidone mesylate. Encapsulating the ziprasidone in cyclodextrin supplies the drug in a dissolved (encapsulated) form at the skin/formulation interface. This may enhance the absorption of the drug into the skin. The encapsulated drug may be incorporated into an emulsion or a hydrogel base.

The antipsychotic topical composition of this invention may be administered once to several times daily. The appropriate volume of the topical composition required to deliver the appropriate dose is then applied to the patient's skin, which is generally a thin layer on an area of about 1 to 5 square inches. The composition is preferably to the patient's neck or wrist.

Thus, in one embodiment, the transdermal composition includes an antipsychotic and a pharmaceutically acceptable carrier. In an alternate embodiment, the transdermal composition of antipsychotic and a pharmaceutically acceptable carrier additionally includes an effective amount of ziprasidone to treat a neuropsychiatric disorder. In yet another embodiment, the transdermal composition also includes antipsychotic in an amount from 0.01 to 25% by weight. In a preferred embodiment of the transdermal composition, the antipsychotic is present in an amount from about 5 to 20% by weight, and more preferably from about 10 to 15% by weight.

The invention also includes methods of topically applying a therapeutically effective amount of antipsychotic for treatment of a neuropsychiatric disorder. In a preferred embodiment, the neuropsychiatric disorder is schizophrenia. In one embodiment, a method of treating a neuropsychiatric disorder in a patient includes identifying a patient having a neuropsychiatric disorder and topically applying a therapeutically effective amount of antipsychotic.

In an alternate embodiment, the method of treating a neuropsychiatric disorder in a patient includes applying a transdermal composition comprising an effective amount of an antipsychotic and a pharmaceutically acceptable carrier. In yet another embodiment, the method for treating a neuropsychiatric disorder in a patient includes applying a transdermal composition comprising an effective amount of an antipsychotic and a pharmaceutically acceptable carrier wherein the carrier as mentioned infra, can include the composition be delivered in the form of aerosol sprays, sprays, powders, sticks, granules, creams, pastes, dispersions, gels, lotions, emulsions, suspensions, syrups, ointments, sponges, cotton applicators, topical dressing, dermal patch, cleansing tissues, solutions, suspensions in an aqueous liquid, a non-aqueous liquid, oil-in-water emulsions, or water-in-oil liquid emulsions.

Another preferred embodiment encompassed in the method of the present invention includes the application of an antipsychotic in an amount from about 0.01 to 99% by weight. In a preferred embodiment, the amount of antipsychotic used to treat a neuropsychiatric disorder in a patient is present in an amount from about 5 to 20% by weight, and more preferably from about 10 to 15% by weight.

The topical antipsychotic formulations of this invention deliver a "hybrid-like" activity ranging between that of the IM injection and oral formulations. Studies conducted using topical ziprasidone demonstrate an onset of action of about 30 minutes. Compilation of data obtained from case reports suggests that topical antipsychotics are suitable for use in both acute agitation/psychotic episodes as well as in the maintenance and treatment of the various neuropsychiatric disorders already discussed. For treatment of acute agitation/psychotic episodes, 40 mg of topical ziprasidone may be initially applied for instance, then the same dose repeated if necessary. For maintenance, ziprasidone may be applied, for instance, in a dose of 40 mg twice daily. As persons skilled in the art well understand, these suggested doses may vary according to a wide range of factors including height and weight of the patient, individual patient response, thickness of the patient's skin, etc.

Studies conducted using the topical antipsychotic demonstrated a marked increase in the alleviation of agitation associated with Alzheimer's disease and schizophrenia versus that achieved using conventional treatments, including oral and IM ziprasidone.

The transdermal composition may be used alone or in conjunction with another anti-psychotics or neuropsychiatric medicinals to manage anti-psychotic symptoms. All references disclosed herein are hereby incorporated by reference in their entireties as if each was incorporated individually.

The following examples are offered to illustrate but not limit the invention. Thus, they are presented with the understanding that various formulation modifications as well as method of delivery modifications may be made and still be within the spirit of the invention.

EXAMPLE 1

Preparation of Ziprasidone HCl in a 10% Topical Suspension Formulation

The present formulation describes the combination of Geodon® capsules containing 80 mg of ziprasidone hydrochloride (HCl) monohydrate, in addition to an unknown percentage of the following ingredients, which may or may not significantly contribute to clinical efficacy: lactose, pregelatinized starch, and magnesium stearate.

Capsule contents are added to a combination of ethoxy diglycol (diethylene glycol monoethyl ether, Transcutol P) which serves a wetting agent for the active ingredient ziprasidone hydrochloride and penetration enhancer and a pre-made lecithin soya:isopropyl palmitate (1:1 w/w) mixture that is preserved using 0.1% (w/w) sorbic acid. The Lecithin Soya is a phospholipid surfactant that serves as the primary emulsifier and also advantageously functions a known penetration enhancer. Soya lecithin is a compilation of various lecithins (neutral or charged) which is determined using a certificate of analysis. The inventor contemplates that a refined phospholipid may also be used rather than lecithin soya to minimize complications arising from the non-uniform composition of lecithin soya. Isopropyl Palmitate constitutes the lipid phase of the emulsion and performs as a known penetration enhancer which imparts appreciable spreadability on the formulation. Lastly, poloxamer 407 (Pluronic F127) is added as a 22% w/v solution (preserved with 0.1% (w/v) potassium sorbate) to constitute the remaining volume (desired volume) of the emulsion and mixed under high shear using a combination of an attached syringe system and subsequent homogenization using an ointment mill. Poloxamer 407 is a polyethylene-polypropylene-polyethylene tri-block copolymer, a non-ionic surfactant with gelation abilities in aqueous solutions of 15% or higher and works in the composition as a secondary emulsifier and emulsion stabilizer. Distilled water may be added to the pluronic to form a 22% solution (gel) to constitute the remaining volume of the emulsion. The final concentration in the prepared mixture is as follows: ziprasidone hydrochloride monohydrate: 10% (w/v), ethoxy diglycol: 22% (v/v), lecithin soya: 7% (w/v), isopropyl palmitate: (7% w/v), poloxamer 407: (8.8% w/v), water (distilled) is added to the pluronic to form a 22% solution (gel) to constitute the remaining volume of the emulsion.

EXAMPLE 2

Preparation of Ziprasidone HCl in a 10% Topical Cream Formulation

Isopropyl palmitate (20% w/w) is combined with Brij 97 (20% w/w) (polyoxyl 10 oleyl ether, brij 96, oleth-10, polyethylene glycol monooleyl ether, valpo 10), glyceryl monooleate (5% w/w), and ziprasidone HCl (10% w/w). The resulting dispersion is heated to approximately 50° C. and mixed under high speed stirring (400 rpm) using a magnetic stir bar for one hour. Water, previously heated to 60° C. is added to the dispersion and mixed well until cooled. The final mixture is subsequently milled.

EXAMPLE 3

Preparation of Ziprasidone Mesylate in a Topical Cyclodextrin Formulation

Ziprasidone mesylate and sulfobutylether β-cyclodextrin are concomitantly combined in a suitable solvent, which is then evaporated to yield a complex of the two additives. The complex is reconstituted with water and incorporated into a pharmaceutically acceptable base.

EXAMPLE 4

Case Study—Use of Topical Ziprasidone for Senile Dementia with Delusions and Psychosis A case study was performed by Dr. Matthew Targoff, D.O. over the course of six days using topical ziprasidone for treatment of a patient having senile dementia with delusions and psychosis.

The patient had increased hallucinations and delusions with irritability secondary to dementia. The patient was inpatient for treatment. Ziprasidone gel was used on at least two occasions during the hospital course on an as needed basis for agitation with hallucinations and delusions and the result was that the patient was calmer and on one occasion in early am was able to go to sleep and slept through the night after being awake and agitated with hallucinations and talking to himself/herself. Seemed to be calmer following both applications of gel.

Onset of action—within 40-50 minutes

Side effects—none noted

Skin irritation—none noted

Ease of application—no problems with application of gel

Dose of ziprasidone in gel—40 mg

EXAMPLE 5

Case Study—Use of Topical Ziprasidone for Senile Dementia with Depression and Behavior Disturbance A case study was performed by Dr. Matthew Targoff, D.O. using topical ziprasidone over the course of about a month for treatment of a patient having senile dementia with depression and behavior disturbance.

This patient had severe agitation and physical aggressiveness to self and other residents, depressed, wanted to be killed or asked people to kill him/her. Hitting himself/herself and combative with others. The patient had several inpatient admissions and was very difficult to manage in nursing home and in hospital. The patient tolerated several medications in combination. At the time of discharge the patient was taking ziprasidone gel 40 mg at 2 and 8 pm. The patient was on other antipsychotic meds as well as other psychotropics on a regular basis. The patient was improved from the time of admission in the patient's degree, frequency, and severity of the patient's combative episodes. He/she was in a better mood and the patient's affect was brighter at the time of discharge. The patient still had episodes of agitation on occasion and needed a combination of ziprasidone gel 40 mg and Ativan® gel 2.0 mg as needed and this helped. This was in addition to the patient's routine oral ziprasidone (Geodon®).

Onset of action—about 45 minutes
Side effects—none noted
Skin irritation—none noted
Ease of application—no problems
Dose of ziprasidone in gel—40 mg

EXAMPLE 6

Case Study—Use of Topical Ziprasidone for Senile Dementia with Depression and Psychotic Features A case study is being performed by Dr. Matthew Targoff, D.O. using topical ziprasidone beginning Mar. 24, 2005 and still continuing for treatment of a patient having senile dementia with depression and psychotic features.

This patient was admitted to the hospital as a result of being extremely anxious, restless, combative, and unmanagement at the nursing home. The patient was not eating, was unable to sit still, having insomnia, and not doing well on the patient's current meds. He/she was given ziprasidone gel 40 mg at 8 p.m. and in combination with alprazolam 0.5 mg at 8 a.m. and 8 p.m. became more manageable and less anxious. The patient also benefitted from an as needed dose of Ativan® gel 2 mg. Sleep improved and the patient's appetite has also improved.

Onset of action—35-40 minutes
Side effects—none noted
Skin irritation—none noted
Ease of application—no problems
Dose of ziprasidone in gel—40 mg

EXAMPLE 7

Case Study—Use of Topical Ziprasidone for Senile Dementia with Delusions and Behavior Disturbance A case study was performed by Dr. Matthew Targoff, D.O. using topical ziprasidone over the course of a week for treatment of a patient having senile dementia with delusions and behavior disturbance.

This patient was hospitalized with delusions surrounding people being in his/her room, taking the patient's items, and seeing people and animals that were not there. He/she also was attempting to elope from the facility and was not redirectable. The patient's meds were changed to include ziprasidone gel 40 mg at 8 p.m. and ziprasidone orally 40 mg (Geodon®) at 8 a.m. The patient was also taking two other antipsychotics at the time of discharge. The patient's behaviors improved and the patient had less delusions and they were less intrusive than at the time of admission. The patient was also more redirectable and reasonable when he/she left.

Onset of action—40 minutes
Side effects—none noted
Skin irritation—none noted
Ease of application—no problems
Dose of ziprasidone in gel—40 mg

EXAMPLE 8

Case Study—Use of Topical Ziprasidone for Senile Dementia with Behavior Disturbance and Delusions A case study is being performed by Dr. Matthew Targoff, D.O. using topical ziprasidone over the course of two weeks for treatment of a patient having senile dementia with behavior disturbance and delusions.

This patient was admitted for the fifth time in a four-week period to the hospital due to extreme combative and aggressive behaviors. The patient was striking out and hitting the staff during cares and had stabbed a staff member with a fork. The patient was also aggressive during cares. The patient was given a routine dose of ziprasidone gel 40 mg at 6 a.m. to keep the patient manageable before cares and was also given ziprasidone 60 mg orally (Geodon®) at bedtime. The patient was also given Ativan® 2 mg gel every a.m. and on an as needed basis. The patient was less combative with these gels and many times did not swing out or strike out at all. The patient had demonstrated improvement in his/her combative behavior, irritability and mood at the time of discharge. The patient was also taking other psychotropic medications with the ziprasidone on a routine basis.

Onset of action—35-40 minutes
Side effects—none noted
Skin irritation—none noted
Ease of application—no problems
Dose of gel: ziprasidone 40 mg and Ativan® 2 mg

EXAMPLE 9

Preparation of Quetiapine Fumarate in a Topical Suspension Formulation

The present formulation describes the combination of Seroquel® tablets containing 200 mg of quetiapine (in the form of quetiapine fumarate salt), in addition to an unknown percentage of the following ingredients, which may or may not significantly contribute to clinical efficacy: povidone, dibasic dicalcium phosphate dihydrate, microcrystalline cellulose, sodium starch glycolate, lactose monohydrate, magnesium stearate, hypromellose, polyethylene glycol and titanium dioxide. The ingredients of the formulation and their amounts are as follows:

| | |
|---|---|
| Seroquel 200 mg tablets | 10 tabs |
| Ethoxy diglycol | 1.6 mL |
| Dimethyl sulfoxide | 1.6 mL |
| Lecithin | 2.4 g |
| Isopropyl palmitate | 2.4 mL |
| Pluronic F127 30% (premade aqueous gel) | |

The Seroquel tablets are crushed using a mortar and pestle. This powder is then passed through a 40 mesh sieve 3. This powder is then wetted with ethoxy diglycol, which serves as a wetting agent for the active ingredient quetiapine and penetration enhancer, and a pre-made lecithin soya:isopropyl palmitate (1:1 w/w) mixture. Lastly, poloxamer 407 (Pluronic F127) is added and mixed to a volume of 16 mL. The product is then passed through an ointment mill to enhance consistency.

It should be appreciated that minor modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A pharmaceutical composition for treatment of neuropsychiatric disorders consisting of: a neuropsychiatric disorder therapeutically effective amount of an antipsychotic, said antipsychotic encapsulated in cyclodextrin, and a dermatologically acceptable carrier; said antipsychotic being selected from the group consisting of ziprasidone and quetiapine; said dermatologically acceptable carrier consisting of ethoxy diglycol, lecithin soya, isopropyl palmitate, poloxamer 407, and water; and further providing that the carrier is selected from the group consisting of cream, paste, dispersion, gel, lotion, emulsion, suspension, syrup, ointment, solution, and liquid.

2. The composition of claim 1 whereby the antipsychotic is present in an amount of from about 0.01% to about 25% by weight.

3. The composition of claim 2 whereby the antipsychotic is present in an amount of from about 10% to about 15% by weight.

4. The composition of claim 1 whereby the antipsychotic is quetiapine.

* * * * *